United States Patent [19]

Vogt et al.

[11] 4,172,053
[45] Oct. 23, 1979

[54] CATALYST FOR REDUCING CARBON MONOXIDE

[75] Inventors: Wilhelm Vogt, Hürth-Efferen; Hermann Glaser, Erftstadt-Lechenich; Jürgen Koch, Brühl, all of Fed. Rep. of Germany

[73] Assignee: Hoechst Aktiengesellschaft, Hürth-Knapsack, Fed. Rep. of Germany

[21] Appl. No.: 917,856

[22] Filed: Jun. 22, 1978

Related U.S. Application Data

[63] Continuation of Ser. No. 732,017, Oct. 13, 1976, abandoned.

[30] Foreign Application Priority Data

Oct. 17, 1975 [DE] Fed. Rep. of Germany ....... 2546587

[51] Int. Cl.² .................... B01J 21/04; B01J 21/08; B01J 23/72; B01J 23/74
[52] U.S. Cl. ........................ 252/447; 252/455 R; 252/459; 252/466 J; 252/472; 252/474
[58] Field of Search ............... 252/447, 455 R, 459, 252/466 J, 472, 474; 260/449 R, 449.6 R, 449.6 M

[56] References Cited

U.S. PATENT DOCUMENTS

| | | | |
|---|---|---|---|
| 2,533,071 | 12/1950 | Vesterdal et al. | 252/472 X |
| 2,753,367 | 7/1956 | Rottig et al. | 252/474 X |
| 2,960,518 | 11/1960 | Peters | 260/449.6 |
| 3,842,121 | 10/1974 | Ichikawa et al. | 252/474 X |

*Primary Examiner*—W. J. Shine
*Attorney, Agent, or Firm*—Connolly and Hutz

[57] ABSTRACT

Reduction of carbon monoxide by means of hydrogen with the resultant formation of a mixture of hydrocarbons having substantially from 1 to 4 carbon atoms in contact with a catalyst containing iron or a mixture of iron and copper as its catalytically active ingredient, the catalyst being made by contacting one or more complex salts of the following general formula:

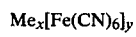

$$Me_x[Fe(CN)_6]_y$$

in which Me stands for an iron and/or copper-ion, x stands for a number of 1 to 4, and y stands for a number of 1 to 3, with hydrogen or a hydrogen/carbon monoxide-mixture at about 200° to 500° C., under 1 to 100 atmospheres absolute and over a period of about 2 to 20 hours and thereby reducing the complex salts substantially to elementary iron or copper.

8 Claims, No Drawings

CATALYST FOR REDUCING CARBON MONOXIDE

This application is a continuation of application Ser. No. 732,017 filed Oct. 13, 1976 now abandoned.

This invention relates to a catalyst containing iron or a mixture of iron and copper as its catalytically active ingredient, and to a process for reducing carbon monoxide by means of hydrogen with the resultant formation of a mixture of hydrocarbons containing substantially from 1 to 4 carbon atoms.

Ethylene is one of the most important lower hydrocarbons which are used as starting materials in the chemical industries for the commercial production of a wide variety of secondary products. In view of the considerable demand for ethylene, it is highly desirable to exploit raw material sources other than petroleum for making ethylene. One of such raw materials which recommend themselves is water gas which is obtained by reacting coal with steam at high temperatures.

The catalytic hydrogenation of carbon monoxide with the resultant formation of hydrocarbons has been fully described, for example, by Winnacker-Weingaertner in "Chemische Technologie", vol. Organische Technologie I, pages 780–803, published by Carl Hauser Verlag, München, 1952. This reaction entails the formation of all hydrocarbons belonging to the olefin and paraffin series, which are obtained in quite different proportions depending on the particular catalyst and reaction conditions used. It is more specifically stated at page 786 of the above publication that in those cases in which an iron or iron/copper-catalyst is substituted for a cobalt catalyst in the hydrogenation of carbon monoxide, olefins tend to be formed at an increasing rate while methane tends to be formed at a decreasing rate. The prior art catalysts are so-called precipitation catalysts. They are made, for example, by dissolving the metals in nitric acid and rapidly precipitating them, while hot, with an alkali metal carbonate solution. After precipitation, the precipitate is filtered off, washed out with water, dried at 110° C., crushed and screened. Next, the screened matter is reduced by contacting it with hydrogen or synthetic gas at 225° C. under a pressure of 10 atmospheres gauge.

The iron or iron/copper-catalysts prepared in the manner just described have an unsatisfactory catalytic efficiency in the hydrogenation of carbon monoxide inasmuch as the reaction gas contains an unsufficiently low proportion of $C_2$–$C_4$ hydro-carbons, especially $C_2$-hydrocarbons. In other words, the catalysts are insufficiently selective as regards the formation of low olefinic hydrocarbons.

The present invention obviates the disadvantageous effects referred to hereinabove and provides iron/copper-catalysts which by reason of the specific method selected for their preparation enable the proportion of $C_2$–$C_4$ hydrocarbons in the reaction gas obtained on hydrogenating carbon monoxide to be considerably increased.

The present invention thus provides more specifically a catalyst containing iron or a mixture of iron and copper as its catalytically active ingredient for reducing carbon monoxide by means of hydrogen with the resultant formation of a mixture of hydrocarbons having substantially from 1 to 4 carbon atoms, said catalyst being made by contacting one or more complex salts of the following general formula:

$$Me_x[Fe(CN)_6]_y$$

in which Me stands for an iron and/or copper-ion, x stands for a number of 1 to 4, and y stands for a number of 1 to 3, with hydrogen or a hydrogen/carbon monoxide-mixture at temperatures of about 200° to 500° C., under pressures of 1 to 100 atmospheres absolute and over a period of about 2 to 20 hours and thereby reducing the complex salts to elementary iron or copper.

In the above general formula, the parameters x and y stand more preferably for the numbers 2 and 4 or 1 and 3, respectively. The particular compounds concerned in this case have approximately the following constitution:

$$Fe_4[Fe(CN)_6]_3, \ CuFe[Fe(CN)_6], \ Cu_2[Fe(CN)_6], \ Cu_4[Fe(CN)_6]$$

in which the water of hydration and residual alkali metal contents remain unmentioned.

A preferred form of catalyst preparation comprises contacting the complex salts with at least stoichiometric proportions of hydrogen or a hydrogen/carbon monoxide-mixture in a preferred molar ratio of 3:1 to 1:2 at temperatures of 350° to 400° C., under pressures of 5 to 50 atmospheres gauge, and over periods of 3 to 10 hours.

With respect to the nature of the catalyst, it is possible for it to be used in the form of granules or pellets or to be deposited on a carrier, such as alumina, silicic acid, kieselguhr, asbestos, glass fibers, clay minerals, pumice or active carbon. In those cases in which the catalyst is deposited on a carrier, it is preferable for about 20 to 95 weight % of catalytically active ingredient to be applied to the carrier, the percentage being based on the total weight of catalytically active ingredient and carrier. The catalyst of the present invention is a precipitation catalyst and it is accordingly possible to obtain the complex salts of the above general formula by precipitating them from an aqueous alkali metal ferrocyanide solution by means of an aqueous solution of an iron and/or copper-salt, and separating and drying the precipitated salt.

The present invention also provides a process for the catalytic reduction of carbon monoxide by means of hydrogen with the resultant formation of a mixture of hydrocarbons containing substantially from 1 to 4 carbon atoms by contacting a carbon monoxide/hydrogen-mixture at elevated temperature, at atmospheric or higher pressure with a catalyst containing iron or a mixture of iron and copper as its catalytically active ingredient and being deposited on a carrier, if desired, which process comprises: contacting the gas mixture containing hydrogen and carbon monoxide in a molar ratio of 0.5–3:1 at temperatures of about 200° to 500° C. and, optionally, under pressures of 1 to 100 atmospheres absolute, with a catalyst, the gas mixture being used at a rate of about 100 to 10,000 normal liter (S.T.P.) per liter of catalyst per hour, and separating hydrocarbons having from 1 to 4 carbon atoms from the issuing gas, said catalyst having been made by contacting one or more complex salts of the following general formula:

$$Me_x[Fe(CN)_6]_y$$

in which Me stands for an iron and/or copper-ion, x stands for a number of 1 to 4, and y stands for a number of 1 to 3, with hydrogen or a hydrogen/carbon monoxide mixture at temperatures of about 200° to 500° C., under pressures of 1 to 100 atmospheres absolute and over a period of about 2 to 20 hours and thereby reducing the complex salts to elementary iron or copper.

A preferred feature of the present process provides for the gas mixture to contain hydrogen and carbon monoxide in a molar ratio of 0.8–3:1 and to be contacted at 250° to 450° C. under pressures of 5 to 50 atmospheres gauge with the catalyst at a rate of 200 to 5000 normal liter per liter of catalyst per hour.

The following statements are intended further to illustrate the catalyst and process of the present invention.

The catalyst can be prepared, for example, by precipitating copper ferrocyanide from an aqueous copper-II-salt-solution by means of an aqueous solution of potassium ferrocyanide. The resulting red-brown precipitate is suction-filtered, washed and dried. Next, the precipitate is reduced in a copper-lined steel tube at 350°–400° C. over a period of about 2 hours with the use of hydrogen.

Another method of preparing a very good hydrogenation catalyst comprises producing an almost white precipitate from an ammoniacal solution of copper-I-chloride and potassium ferrocyanide (molar ratio=4:1), drying the precipitate and reducing it by means of hydrogen.

A still further method of preparing an effective hydrogenation catalyst comprises reacting an aqueous solution of a copper-II-salt and iron-II-salt with potassium ferrocyanide in a molar ratio of 1:1:1, separating the resulting black-blue precipitate, drying the precipitate and reducing it with hydrogen. The black-blue precipitate contains iron and copper in an atomic ratio of 1:2. If the atomic ratio of Cu:Fe is further reduced, the catalyst becomes less selective relative to the formation of $C_2$-hydrocarbons. Even those catalysts, which are prepared from ferricyanide and ferrocyanide, have however been found to possess good hydrogenating properties.

The catalysts prepared in the manner described hereinabove can, for example, be applied to a carrier by precipitating the complex cyanides in an aqueous suspension of the carrier, separating the resulting mixture of precipitated cyanide and carrier, drying the mixture, washing it and reducing the cyanides by means of hydrogen at the necessary temperature.

Another method of applying the catalyst to the carrier comprises impregnating preformed carrier material with the complex cyanides by first impregnating the carrier with an aqueous solution of potassium ferrocyanide, then drying the carrier so impregnated and reacting the carrier with an aqueous solution of a copper salt.

A still further method comprises mixing the aqueous solution of potassium ferrocyanide with a copper salt in the presence of ammonia (precipitation is obviated, e.g. in those cases in which a copper-II-salt and potassium ferrocyanide are used), impregnating the carrier with the resulting solution and precipitating the copper-cyanide complex by evaporation of the ammonia.

It is not absolutely necessary for the dry catalyst to be treated with hydrogen. It may well be contacted immediately with the CO/$H_2$-mixture at the necessary reaction temperature to effect reduction of the cyanide complex. A catalyst so prepared was taken after about 8 hours of operation from a reactor and found to be pyrophorous in contact with air. The nitrogen content of the catalyst was found to have dropped to about 0.2–0.4 weight %, i.e. the complex cyanide compound was found to have been extensively destroyed.

As more fully illustrated in the following Examples, the present iron/copper catalysts compare favorably with the prior art catalyst in respect of the following points: They can be prepared under commercially attractive conditions and combine this with a relatively high selectivity in the reaction of carbon monoxide with hydrogen with the resultant formation of $C_1$–$C_4$ hydrocarbons.

EXAMPLE 1

Particulate pumice (particle size=2–3 mm) was introduced into an aqueous solution of potassium ferrocyanide saturated while hot, supernatant liquid was poured off, the remaining material was dried and mixed with a $FeCl_3$-solution in excess. The resulting blue mass was water-washed and dried in a drying cabinet at 120° C. 30 g of the product so obtained was placed in a copper-lined tube 16 mm wide and reduced by means of hydrogen over a period of 3 hours at 250°–300° C. under a pressure of 5 atmospheres gauge.

The catalyst so made was contacted with 30 normal liter/hr of a $H_2$/CO-mixture (molar ratio=1:1) under a pressure of 10 atmospheres gauge. The reaction temperature was 385° C. The gas issuing from the reactor contained 1.8% by volume of ethylene and ethane, 7.2% by volume of methane, 1% by volume of $C_3$ hydrocarbons and 0.8% by volume of $C_4$ hydrocarbons. Liquid hydrocarbons could not be found to have been formed. The hydrogenation was accompanied by the formation of $CO_2$.

The experiment was repeated under the reduction conditions described, but the molar ratio of $H_2$:CO=1:1 was changed to 3:1. The quantity of $C_2$, $C_3$ and $C_4$ hydrocarbons remained unchanged, but 9.3% by volume of $CH_4$ was obtained. Less $CO_2$ was found to have been formed in favor of water.

EXAMPLE 2

The procedure was as described in Example 1, but granular pumice was charged with $K_4[Fe(CN)_6]$ and the granular material was introduced into an aqueous solution of copper and iron sulfates (molar ratio=1:1). The cyanide complex applied to the granular pumice corresponded approximately to the following formula $CuFe[Fe(CN)_6]$. The dry granular material was contacted with 30 normal liter/hr of a $H_2$/CO-mixture (molar ratio=1:1) at 345° C. under a pressure of 9.5 atmospheres gauge. The gas issuing from the reactor contained 2.4% by volume of $C_2$ hydrocarbons, 1.3% by volume of $C_3$ hydrocarbons, 1.1% by volume of $C_4$ hydrocarbons and 6.4% by volume of methane.

EXAMPLE 3

0.5 mol of $K_4[Fe(CN)_6]$ was dissolved in a suspension of 90 g of most finely divided silicic acid (AEROSIL, a product of Degussa, Frankfurt/Main) in 2 liter of water. Next, a solution of 0.5 mol of $CuSO_4$ and 0.5 mol of $FeSO_4$ was stirred thereinto. The resulting precipitate was filtered off together with silicic acid, thoroughly washed with water and dried. 30 g of the product so obtained was contacted at 340° C. and under a pressure of 9.5 atmospheres gauge with 30 normal liter/hr of a $H_2$/CO-mixture (molar ratio=1:1). The issuing gas contained 4.4% by volume of $C_2$ hydrocarbons, 2.2% by volume of $C_3$ hydrocarbons, 1.2% by volume of $C_4$ hydrocarbons and 13.2% by volume of methane. Liquid higher hydrocarbons could not be found to have been formed. The reaction was accompanied by the formation of $CO_2$.

EXAMPLE 4

The procedure was as described in Example 3, but the water-washed mixture was mixed with agitation with 5 weight %, based on the dry mixture, of potassium waterglass, which was a 28 weight % aqueous solution, the whole was dried and comminuted. The dry product was contacted at 360° C. with a $H_2$/CO-gas mixture to effect reduction of the cyanide complex to the catalytically active material. The resulting reaction gas contained 3.5% by volume of $C_2$ hydrocarbons together with 9.6% by volume of $CH_4$.

EXAMPLE 5

The procedure was as described in Example 3, but the AEROSIL silicic acid was replaced by hydrate of alumina (a commercially available product of Condea Petrochemie Gesellschaft mbH, Brunsbüttel). The reaction temperature was 315° C. The reaction gas contained 2.8% by volume of $C_2$ hydrocarbons together with 7.8% by volume of methane.

EXAMPLE 6

An aqueous solution of 2 mol of $CuSO_4$ was mixed with agitation with an aqueous solution of 1 mol of $K_4[Fe(CN)_6]$ and copper ferrocyanide corresponding approximately to the formula $Cu_2[Fe(CN)_6]$ was found to have been precipitated. The precipitate was filtered off, washed with water, dried and tabletted. 30 g of the tabletted material was contacted at 360° C. and under a pressure of 9.5 atmospheres gauge with 30 normal liter/hr of a $H_2$/CO-mixture. The resulting reaction gas contained 2.66% by volume of $C_2$ hydrocarbons and 11.7% by volume of methane. The hydrogenation was accompanied by the formation of water.

EXAMPLE 7

An aqueous copper sulfate solution was introduced into an aqueous solution of potassium ferrocyanide, which had fine particulate pumice suspended therein, to cause precipitation of copper ferrocyanide which was deposited on the pumice. The mixture of pumice and copper ferrocyanide was filtered off, washed with water and dried at about 60° C. 30 g of the product so obtained was contacted at 320° C. under a pressure of 9.5 atmospheres gauge with 30 normal liter/hr of a $H_2$/CO-mixture (molar ratio=3:1). The resulting reaction gas contained 3% by volume of $C_2$ hydrocarbons and 10.5% by volume of methane. The oxygen contained in the CO-gas which underwent reaction was converted to $CO_2$.

EXAMPLE 8

90 g of AEROSIL was suspended in a solution of 0.5 mol of $K_4[Fe(CN)_6]$ in 2 liter of water. The suspension was admixed with agitation with a solution of 1 mol of $CuSO_4$ and 2 liter of water and $Cu_2[Fe(CN)_6]$ was precipitated. The suspension was filtered, the filter residue was washed with water and dried. The dry product was contacted at 320° C. under a pressure of 9.5 atmospheres gauge with 30 normal liter/h of a CO/$H_2$-gas mixture (molar ratio of $H_2$:CO=1:1). After reduction of the dry product to catalytically active material, the catalyst produced a reaction gas which contained 2.7% by volume of $C_2$ hydrocarbons, 1.5% by volume of $C_3$ hydrocarbons, 0.7% by volume of $C_4$ hydrocarbons and 4.6% by volume of $CH_4$.

EXAMPLE 9

The procedure was as described in Example 8 but $Al_2O_3$ was substituted for the AEROSIL carrier. (The $Al_2O_3$ used was a product of Degussa, Frankfurt/Main, commercially available under the designation "Aluminiumoxid C"). The resulting reaction gas contained 3.5% by volume of $C_2$ hydrocarbons and 11.5% by volume of $CH_4$.

EXAMPLE 10

0.5 mol of $Cu(NO_3)_2$ was dissolved in water, admixed with ammonia and the resulting deep blue solution was decolorized by means of hydroxyl amine hydrochloride. Next, the solution was admixed with 0.125 mol of $K_4[Fe(CN)_6]$ in 200 ml of water. The resulting white precipitate of the approximate formula $Cu_4[Fe(CN)_6]$ was filtered off, washed with water, dried and tabletted. 30 g of the tabletted product was contacted at 340° C. under a pressure of 9.5 atmospheres gauge with 30 normal l/hr of a $H_2$/CO-mixture (molar ratio=1:1). The resulting reaction gas contained 2.5% by volume of $C_2$ hydrocarbons and 10% by volume of $CH_4$.

EXAMPLE 11

1.2 mol of $Cu(NO_3)_2$ was dissolved in water, admixed with ammonia and the resulting deep blue solution was decolorized by means of hydroxyl amine sulfate. 90 g of AEROSIL was suspended in the solution and the resulting suspension was admixed with 0.3 mol of $K_4[Fe(CN)_6]$. The suspension was filtered, the filter residue was washed with water and dried. 30 g of the dry product was contacted at 325° C. under a pressure of 9.5 atmospheres gauge with 30 normal liter/hr of a $H_2$/CO-gas mixture (molar ratio=1:1). The resulting reaction gas contained 2.6% by volume of $C_2$ hydrocarbons and 11.2% by volume of $CH_4$.

EXAMPLE 12

The procedure was as described in Example 11, but the AEROSIL was replaced by alumina (a product of Degussa, commercially available under the designation of "Aluminiumoxid C"). The resulting reaction gas contained 2.5% by volume of $C_2$ hydrocarbons and 9.2% by volume of $CH_4$.

EXAMPLE 13: (Comparative Example)

A hot solution of 1 mol of $Cu(NO_3)_2$, 0.5 mol of $Fe(NO_3)_3$, 6 g of $Zr(NO_3)_4$ in 2 liter of water was admixed with thorough agitation with 2.5 liter of an aqueous solution containing 2 mol of $Na_2CO_3$. Next, the mixture was stirred into 100 g of kieselguhr. The resulting precipitate was suction-filtered, thoroughly washed with water and dried. 30 g of the dry product was reduced by means of hydrogen over a period of 2 hours, at 300° C. and under a pressure of 5 atmospheres gauge. The catalyst so obtained was contacted with 30 liter/hr of a $H_2$/CO-mixture (molar ratio=2:1). The resulting reaction gas contained the following quantities of $C_2$ hydrocarbons, methane and $CO_2$, depending on the reaction temperature used in each particular case.

Table:

| Temp. °C. | Pressure atm. gauge | $C_2$-hydrocarbons % by volume | $CH_4$ % by vol. | $CO_2$ % by vol. |
|---|---|---|---|---|
| 350 | 9.5 | 0.22 | 0.98 | 0.93 |

Table:-continued

| Temp. °C. | Pressure atm. gauge | $C_2$-hydrocarbons % by volume | $CH_4$ % by vol. | $CO_2$ % by vol. |
|---|---|---|---|---|
| 390 | 9.5 | 0.35 | 1.60 | 1.64 |
| 410 | 9.5 | 0.33 | 1.65 | 1.55 |

The water of hydration present in the salts specified in the above Examples and used for making the catalysts has not been identified for reasons of simplicity.

We claim:

1. Catalyst for reducing carbon monoxide by means of hydrogen with the resultant formation of a mixture of hydrocarbons having from 1 to 4 carbon atoms, said catalyst having been made by contacting complex salts of the following general formula:

$$Me_x[Fe(CN)_6]_y$$

in which Me stands for an iron and/or copper-ion, x stands for a number of 1 to 4, and y stands for a number of 1 to 3, with hydrogen or a hydrogen/carbon monoxide-mixture at temperatures of about 200° to 500° C., under pressures of 1 to 100 atmospheres absolute and over a period of about 2 to 20 hours and thereby reducing the complex salts substantially to elementary iron or copper.

2. Catalyst as claimed in claim 1, wherein the parameter x stands for 2 or 4 and the parameter y stands for 1 or 3.

3. Catalyst as claimed in claim 1, the catalyst having been made by contacting the complex salts with at least stoichiometric proportions of hydrogen or a hydrogen/carbon monoxide-mixture at temperatures of 350° to 400° C., under pressures of 5 to 50 atmospheres gauge and over a period of 3 to 10 hours.

4. Catalyst as claimed in claim 1, having been made by contacting the complex salts with a hydrogen/carbon monoxide mixture in a molar ratio of 3:1 to 1:2.

5. Catalyst as claimed in claim 1, the catalyst being in the form of granules or pellets or being deposited on a carrier.

6. Catalyst as claimed in claim 5, wherein the carrier is alumina, silicic acid, kieselguhr, asbestos, glass fibers, clay minerals, pumice or active carbon.

7. Catalyst as claimed in claim 5, wherein about 20 to 95 weight % of catalytically active ingredient is applied to the carrier, the percentage being based on the total weight of catalytically active ingredient and carrier.

8. Catalyst as claimed in claim 1, wherein the complex salts of the general formula are made by precipitating them from an aqueous alkali metal ferrocyanide solution by means of an aqueous solution of an iron and/or copper salt, and separating and drying the precipitated salt.

* * * * *